US011918475B2

(12) United States Patent
Lewis et al.

(10) Patent No.: US 11,918,475 B2
(45) Date of Patent: Mar. 5, 2024

(54) MODULAR ACETABULAR SURGICAL IMPLANT ASSEMBLY

(71) Applicant: DEPUY SYNTHES PRODUCTS, INC., Raynham, MA (US)

(72) Inventors: Paul P. Lewis, Claypool, IN (US); Ian J. Flatters, Leeds (GB)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 89 days.

(21) Appl. No.: 17/219,583

(22) Filed: Mar. 31, 2021

(65) Prior Publication Data

US 2022/0313444 A1 Oct. 6, 2022

(51) Int. Cl.
*A61F 2/30* (2006.01)
*A61F 2/34* (2006.01)
*A61F 2/46* (2006.01)

(52) U.S. Cl.
CPC .............. *A61F 2/34* (2013.01); *A61F 2/4609* (2013.01); *A61F 2002/30011* (2013.01); *A61F 2002/30028* (2013.01); *A61F 2002/3435* (2013.01)

(58) Field of Classification Search
CPC ....... A61F 2/34; A61F 2/4609; A61F 2002/30011; A61F 2002/30028; A61F 2002/3435; A61F 2002/30579; A61F 2002/3401; A61F 2002/3429; A61F 2002/3432; A61F 2/30749
See application file for complete search history.

(56) References Cited

U.S. PATENT DOCUMENTS

| 2,947,308 | A | | 8/1960 | Gorman | |
|---|---|---|---|---|---|
| 3,067,740 | A | * | 12/1962 | Haboush | A61F 2/32 623/22.44 |
| 3,903,549 | A | * | 9/1975 | Deyerle | A61F 2/34 623/22.36 |

(Continued)

FOREIGN PATENT DOCUMENTS

| DE | 102020109617 A1 * | 10/2021 | ......... A61F 2/30749 |
|---|---|---|---|
| EP | 0846453 A2 | 6/1998 | |

(Continued)

OTHER PUBLICATIONS

Machine Translation of DE 102020109617 A1; Schneider; whole document (Year: 2020).*

(Continued)

*Primary Examiner* — Brian A Dukert
*Assistant Examiner* — Melissa A Hoban
(74) *Attorney, Agent, or Firm* — Barnes & Thornburg LLP

(57) ABSTRACT

An orthopaedic prosthetic system includes a plate having one or more flanges and an acetabular shell component. Each flange includes a surface configured to engage a patient's bone. The plate also includes a central ring that engages a lip extending from an outer surface of the shell component. The ring may be mechanically attached to the lip using multiple fasteners. The system may include multiple plates each having a different configuration from other plates, and may also include multiple shell components each having a different configuration from other shell components. Methods for assembling and using the prosthetic system are also disclosed.

14 Claims, 14 Drawing Sheets

(56) References Cited

U.S. PATENT DOCUMENTS

| | | | |
|---|---|---|---|
| 4,623,352 A * | 11/1986 | Oh | A61F 2/34 623/22.28 |
| 5,871,548 A * | 2/1999 | Sanders | A61F 2/34 623/22.36 |
| 6,302,890 B1 | 10/2001 | Leone, Jr. | |
| 6,416,553 B1 * | 7/2002 | White | A61F 2/4637 623/22.38 |
| 6,458,161 B1 | 10/2002 | Gibbs et al. | |
| 6,620,200 B1 * | 9/2003 | Descamps | A61F 2/34 623/22.32 |
| 7,175,664 B1 | 2/2007 | Lakin | |
| 7,207,993 B1 | 4/2007 | Baldwin et al. | |
| 7,393,335 B2 | 7/2008 | Carvey et al. | |
| 7,416,538 B2 | 8/2008 | Katoh et al. | |
| 7,559,909 B2 | 7/2009 | Katoh et al. | |
| 7,641,698 B1 | 1/2010 | Gibbs et al. | |
| 7,780,616 B2 | 8/2010 | Katoh et al. | |
| 7,798,983 B2 | 9/2010 | Katoh et al. | |
| 8,048,166 B2 | 11/2011 | Brown et al. | |
| 8,192,453 B2 | 6/2012 | Valla | |
| 8,439,921 B2 | 5/2013 | Jamali | |
| 8,460,393 B2 | 6/2013 | Smith et al. | |
| 8,696,757 B2 | 4/2014 | Brown et al. | |
| 8,828,089 B1 | 9/2014 | Perez et al. | |
| 8,888,786 B2 | 11/2014 | Stone et al. | |
| 8,906,109 B2 | 12/2014 | Smith et al. | |
| 8,920,351 B2 | 12/2014 | Polliack et al. | |
| 8,926,536 B2 | 1/2015 | Hopman et al. | |
| 9,028,435 B2 | 5/2015 | Hopman et al. | |
| 9,192,478 B2 | 11/2015 | Weeden | |
| RE46,032 E | 6/2016 | Torrie et al. | |
| 9,387,080 B2 | 7/2016 | Boyden et al. | |
| 9,398,955 B2 | 7/2016 | Boyden et al. | |
| 9,402,728 B2 | 8/2016 | Liu et al. | |
| 9,427,238 B2 | 8/2016 | Hopman et al. | |
| 9,468,577 B2 | 10/2016 | Sluss et al. | |
| 9,566,156 B2 | 2/2017 | Monaghan et al. | |
| 9,615,942 B2 | 4/2017 | Smith et al. | |
| 9,883,954 B1 | 2/2018 | Murphy | |
| 10,016,287 B2 | 7/2018 | Murphy et al. | |
| 10,159,520 B2 | 12/2018 | Krickeberg et al. | |
| 10,188,520 B2 | 1/2019 | Smith et al. | |
| 10,188,571 B2 | 1/2019 | Wyslucha et al. | |
| 10,231,739 B1 | 3/2019 | Bonutti | |
| 10,245,149 B2 | 4/2019 | Loffredo | |
| 10,357,391 B2 | 7/2019 | Petursson | |
| 10,456,274 B2 | 10/2019 | Murphy et al. | |
| 2002/0082706 A1 * | 6/2002 | Raugel | A61F 2/0095 623/22.24 |
| 2003/0153982 A1 * | 8/2003 | Pria | A61F 2/34 623/22.24 |
| 2004/0199258 A1 * | 10/2004 | Macara | A61F 2/34 623/22.32 |
| 2004/0225369 A1 * | 11/2004 | Lakin | A61F 2/32 623/22.29 |
| 2006/0058887 A1 * | 3/2006 | DeSmet | A61F 2/34 623/22.36 |
| 2006/0190089 A1 * | 8/2006 | Montoya | A61F 2/34 623/22.32 |
| 2006/0241776 A1 | 10/2006 | Brown et al. | |
| 2008/0161738 A1 | 7/2008 | Giesen | |
| 2008/0172130 A1 * | 7/2008 | Macara | A61F 2/34 623/22.36 |
| 2008/0214976 A1 | 9/2008 | Memminger | |
| 2009/0292369 A1 | 11/2009 | Kazerooni et al. | |
| 2011/0099720 A1 | 5/2011 | Wyslucha et al. | |
| 2011/0213466 A1 | 9/2011 | Shenoy et al. | |
| 2011/0282460 A1 * | 11/2011 | Holtmann | A61F 2/34 623/22.24 |
| 2012/0053699 A1 * | 3/2012 | Meridew | A61F 2/34 623/22.29 |
| 2013/0297036 A1 * | 11/2013 | Collins | A61F 2/34 623/22.24 |
| 2014/0296991 A1 | 10/2014 | Linares et al. | |
| 2014/0336776 A1 * | 11/2014 | Taylor | A61F 2/34 623/22.21 |
| 2017/0112628 A1 * | 4/2017 | Dressler | A61B 17/1668 |
| 2018/0071128 A1 | 3/2018 | Palmer | |
| 2018/0116828 A1 | 5/2018 | Quinn et al. | |
| 2018/0153725 A1 | 6/2018 | Palmer | |
| 2018/0200073 A1 | 7/2018 | Joo et al. | |
| 2018/0271692 A1 | 9/2018 | Palmer | |
| 2019/0053965 A1 | 2/2019 | Woolson | |
| 2019/0076256 A1 | 3/2019 | Macke | |
| 2019/0231217 A1 | 8/2019 | Sadlik et al. | |
| 2020/0205987 A1 * | 7/2020 | Brandewie | A61F 2/34 |
| 2021/0077262 A1 * | 3/2021 | Lee | A61F 2/4609 |

FOREIGN PATENT DOCUMENTS

| | | |
|---|---|---|
| EP | 1377237 A2 | 1/2004 |
| EP | 1845849 A2 | 10/2007 |
| EP | 1874239 A2 | 1/2008 |
| EP | 1388329 B1 | 5/2009 |
| EP | 1605838 B1 | 6/2009 |
| EP | 1637112 B1 | 5/2012 |
| EP | 1637116 B1 | 5/2012 |
| EP | 1301652 B1 | 9/2013 |
| EP | 2502604 B1 | 9/2013 |
| EP | 2200542 B1 | 4/2014 |
| EP | 2410952 B8 | 10/2014 |
| EP | 1637115 B1 | 11/2015 |
| EP | 2995284 A2 | 3/2016 |
| EP | 2623082 B1 | 6/2016 |
| EP | 2897568 B1 | 8/2016 |
| EP | 1889591 B1 | 3/2017 |
| EP | 2699213 B1 | 5/2017 |
| EP | 3228280 A1 | 10/2017 |
| EP | 1889592 B1 | 1/2018 |
| EP | 2996639 B1 | 3/2018 |
| EP | 2505165 B1 | 4/2018 |
| EP | 2688517 B1 | 7/2018 |
| EP | 3484361 A1 | 5/2019 |
| EP | 1742711 B1 | 7/2019 |
| FR | 3004102 A1 | 10/2014 |
| WO | 2010109235 A1 | 9/2010 |
| WO | 2011065378 A1 | 6/2011 |
| WO | 2011117644 A2 | 9/2011 |
| WO | 2011156506 A2 | 12/2011 |
| WO | 2011146617 A9 | 3/2012 |
| WO | 2012103881 A2 | 8/2012 |
| WO | 2013025546 A1 | 2/2013 |
| WO | 2014052151 A1 | 4/2014 |
| WO | 2014094002 A2 | 6/2014 |
| WO | 2014132221 A1 | 9/2014 |
| WO | 2014197451 A1 | 12/2014 |
| WO | 2015018340 A1 | 2/2015 |
| WO | 2015135377 A1 | 9/2015 |
| WO | 2015165817 A1 | 11/2015 |
| WO | 2017010797 A1 | 1/2017 |
| WO | 2017022950 A1 | 2/2017 |
| WO | 2017073458 A1 | 5/2017 |
| WO | 2017098039 A1 | 6/2017 |
| WO | 2017133730 A1 | 8/2017 |
| WO | 2018012990 A1 | 1/2018 |
| WO | 2018219376 A1 | 12/2018 |
| WO | 2019038203 A1 | 2/2019 |
| WO | 2019200174 A1 | 10/2019 |

OTHER PUBLICATIONS

International Search Report for International Application No. PCT/IB2022/052978, dated Jun. 23, 2022, 7 pages.

* cited by examiner

US 11,918,475 B2

MODULAR ACETABULAR SURGICAL IMPLANT ASSEMBLY

TECHNICAL FIELD

The present disclosure relates generally to orthopaedic surgical implants and, more particularly, to modular orthopaedic surgical implant systems.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

From time to time, revision surgery may be performed to replace an acetabular prosthetic component. Oftentimes in revision surgery (or in primary implant surgery), a portion of the patient's hipbone adjacent to the acetabulum is damaged or diseased. To address severe acetabular bone loss, bone quality, bone deformity, or a combination of those, a surgeon may typically use a cemented acetabular cup implant combined with a cage device that attaches to a remaining part of the patient's bone. Such cup and cage constructs typically require use of bone cement and may have limited structural strength. Alternatively, a surgeon may use a patient-specific custom tri-flange acetabular cup implant. Such patient-specific custom implants may have long manufacturing lead times and high expense.

SUMMARY

According to one aspect, an orthopaedic prosthetic system includes a plate and an acetabular shell component. The plate includes a central ring and one or more flanges, wherein a plurality of apertures are defined in the central ring, and wherein each flange of the one or more flanges extends radially away from a corresponding predetermined position on the central ring. Each of the one or more flanges includes a proximal surface to engage a patient's bone. The acetabular shell component includes a distal rim, a convex outer wall extending from the distal rim, and a circumferential lip positioned on the outer wall and extending away from the outer wall. The lip is separated from the distal rim by a lateralization distance, and an inclination angle is defined between a first imaginary plane defined by the lip and a second imaginary plane defined by the distal rim. A plurality of apertures are defined in the lip. The plate is configured to be positioned on the acetabular shell component such that each aperture of the central ring is aligned with a corresponding aperture of the lip of the acetabular shell component.

In an embodiment, the orthopaedic prosthetic system further includes a fastener that, when the plate is positioned on the acetabular shell component, extends through an aperture of the central ring into a corresponding aperture of the lip to secure the plate to the acetabular shell component.

In an embodiment, the outer wall of the acetabular shell component includes an annular outer surface that extends from the distal rim to a hemispherical outer surface, and wherein the lip is positioned on the annular outer surface.

In an embodiment, when the plate is positioned on the acetabular shell component, a proximal surface of the central ring engages a distal surface of the lip, and the central ring receives the distal rim of the acetabular shell component. In an embodiment, the outer wall of the acetabular shell component comprises an annular outer surface that extends from the distal rim to a hemispherical outer surface, and wherein when the plate is positioned on the acetabular shell component a distal surface of the central ring engages a proximal surface of the lip and the central ring receives the hemispherical outer surface of the acetabular shell component.

In an embodiment, the one or more flanges includes an ilial flange configured to engage an ilium of the patient and an ischial flange configured to engage an ischium of the patient.

In an embodiment, the plate is a first plate of a plurality of plates, each plate having a different configuration from other plates of the plurality of plates. In an embodiment, each flange of the one or more flanges of each plate extends radially away from the corresponding predetermined position on the central ring to a corresponding flange end, wherein a flange length is defined between the central ring and the flange end for each flange of the one or more flanges; and the different configuration of each plate includes at least one of the flange length of one or more flange or the predetermined position on the central ring of one or more flange.

In an embodiment, the acetabular shell component is a first shell component of a plurality of acetabular shell components, each acetabular shell component having a different configuration from other acetabular shell components of the plurality of acetabular shell components. In an embodiment, the different configuration of each acetabular shell component includes at least one of the lateralization distance or the inclination angle.

In an embodiment, each of the one or more flanges is malleable. In an embodiment, each of the one or more flanges is nonmalleable. In an embodiment, the proximal surface of each of the one or more flanges and the outer wall of the acetabular shell component includes a porous coating to promote bone ingrowth.

In an embodiment, the plate includes a distal surface and a proximal surface opposite the distal surface, wherein the plurality of apertures extend through the distal surface and the proximal surface.

In an embodiment, a flange of the one or more flanges includes an aperture configured to receive a fastener to attach the flange to the patient's bone.

In an embodiment, the orthopaedic prosthetic system further includes a spacer ring. A plurality of apertures extend through the spacer ring. The spacer ring is configured to be positioned between the lip of the acetabular shell component and the central ring of the plate such that each aperture of the spacer ring is aligned with a corresponding aperture of the lip and a corresponding aperture of the acetabular shell component.

In an embodiment, the acetabular shell component further includes a concave inner wall that extends inwardly from the distal rim to define a cavity sized to receive an acetabular bearing. In an embodiment, the acetabular shell component includes a first subcomponent and a second subcomponent, and wherein the first subcomponent comprises the outer wall and the lip, and the second subcomponent comprises the distal rim and the inner wall; wherein the first subcomponent includes a second concave inner wall that defines a cavity sized to receive the second subcomponent, and wherein the second component is mechanically coupled to the first subcomponent. In an embodiment, the second concave inner wall includes a taper configured to receive the second subcomponent. In an embodiment, the second concave inner wall of the first subcomponent defines a first polar axis; the inner wall of the second subcomponent defines a second polar axis; and a nonzero inclination angle is defined between the first polar axis and the second polar axis.

According to another aspect, a method for assembling an orthopaedic prosthesis includes selecting a first plate from a plurality of plates, wherein each plate of the plurality of plates comprises a central ring and one or more flanges, wherein each flange of the one or more flanges extends radially away from a corresponding predetermined position on the central ring, and wherein each of the one or more flanges includes a proximal surface to engage a patient's bone; selecting a first shell component from a plurality of acetabular shell components, wherein each acetabular shell component of the plurality of acetabular shell components comprises a distal rim, a convex outer wall extending from the distal rim, and a circumferential lip positioned on the outer wall and extending away from the outer wall; and mechanically attaching the lip of the first shell component to the central ring of the first plate.

In an embodiment, a plurality of apertures are defined in the central ring of each plate of the plurality of plates, and a plurality of apertures are defined in the lip of each acetabular shell component of the plurality of acetabular shell components; and mechanically attaching the lip of the first shell component to the central ring of the first plate comprises, for each aperture defined in the central ring, securing a fastener to the aperture of the central ring and to a corresponding aperture of the lip.

In an embodiment, mechanically attaching the lip of the first shell component to the central ring comprises (i) attaching a spacer ring to the central ring and (ii) attaching the spacer ring to the lip.

In an embodiment, selecting first shell component includes selecting a first subcomponent, wherein the first subcomponent comprises the outer wall and the lip of the first shell component; selecting a second subcomponent, wherein the second subcomponent comprises the distal rim and a concave inner wall that extends inwardly from the distal rim; and attaching the first shell subcomponent to the second shell subcomponent.

In an embodiment, the method further includes inserting the first shell component into a surgically prepared acetabulum of a patient in response to mechanically attaching the lip of the first shell component to the central ring of the first plate; and contacting the one or more flanges of the first plate against the patient's bone in response to inserting the first shell component.

BRIEF DESCRIPTION OF THE DRAWINGS

The detailed description particularly refers to the following figures, in which.

DETAILED DESCRIPTION OF THE DRAWINGS

Figure 1:
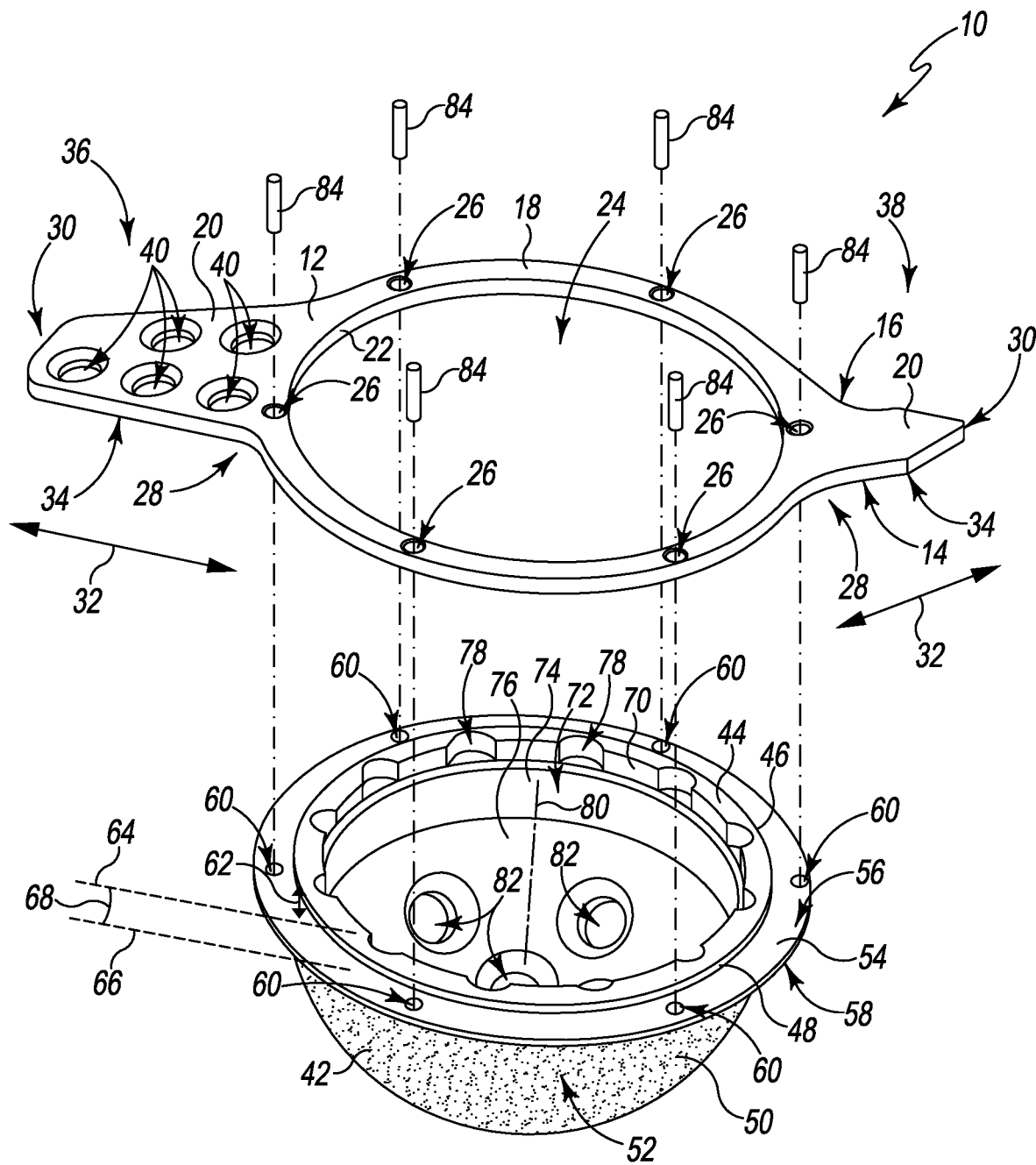
FIG. 1 is an exploded perspective view of an orthopaedic prosthetic system for an acetabular prosthetic implant.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
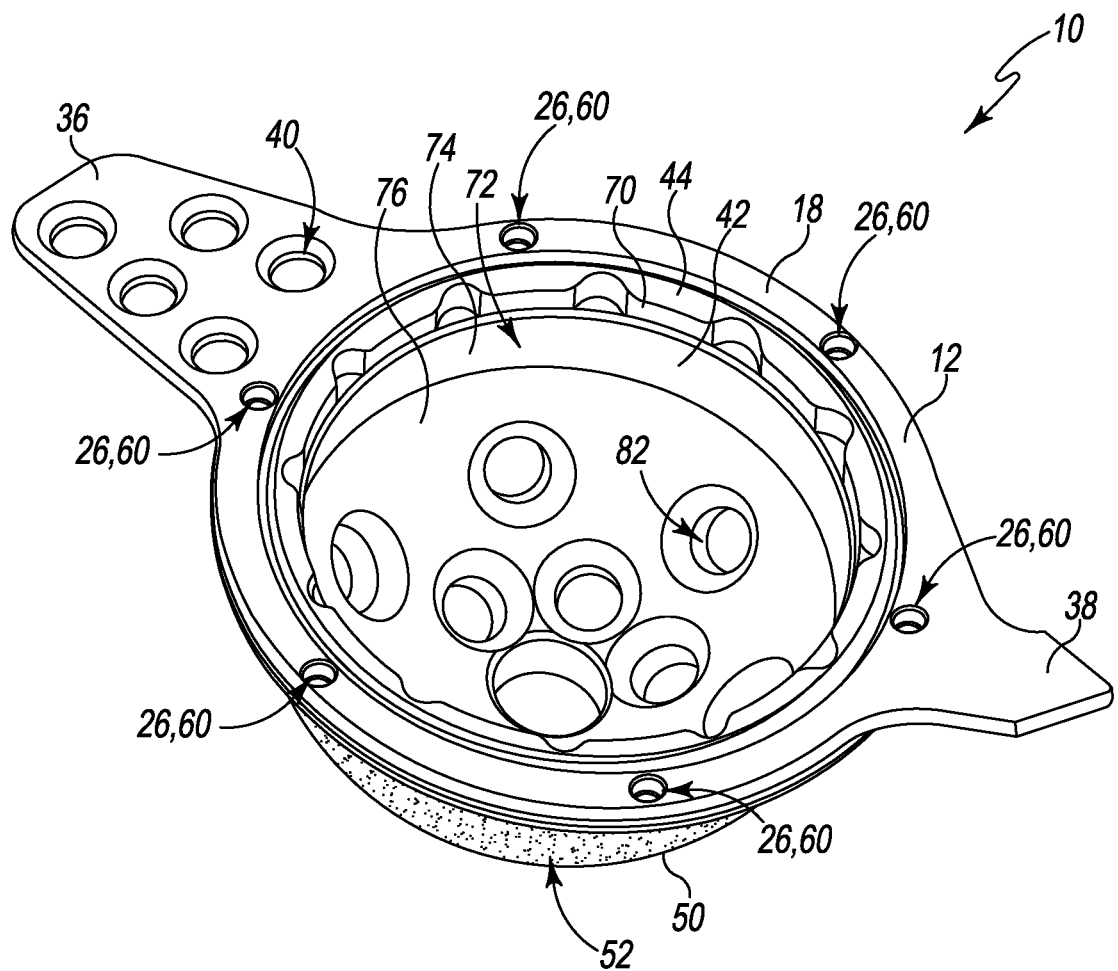
FIG. 2 is a perspective view of an assembled orthopaedic prosthetic system of FIG. 1.
Figure 3:
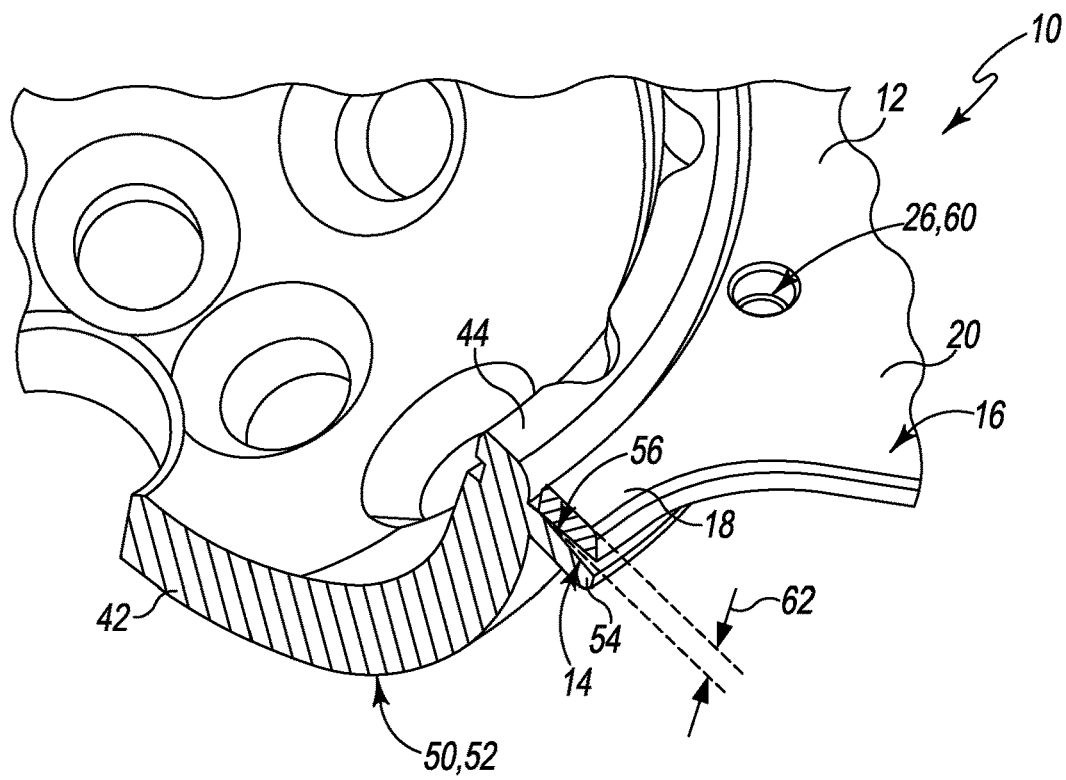
FIG. 3 is a cross-sectional perspective view of the assembled orthopaedic prosthetic system of FIGS. 1-2.

Referring now to FIGS. 1-3, an illustrative acetabular prosthetic implant system 10 includes an anatomic plate 12 and an acetabular shell component 42. The anatomic plate 12 includes a proximal surface 14 opposite a distal surface 16, and is formed from an implant-grade metallic material such as cobalt chromium or titanium. As shown, the anatomic plate 12 includes a central ring 18 that is surrounded by one or more flanges 20. The central ring 18 includes an inner wall 22 that extends between the surfaces 14, 16 and defines an opening 24. As described further below, the opening 24 is sized to receive part of the acetabular shell component 42. Multiple apertures 26 are defined in the central ring 18. The apertures extend through the surfaces 14, 16 of the central ring 18 and are each configured to receive a fastener. For example, in some embodiments, each aperture 26 may include a threaded inner wall that is configured to mate with a threaded body of a screw. As described further below, the apertures 26 and corresponding fasteners may be used to mechanically attach the plate 12 to the shell component 42.

As described above, one or more flanges 20 extend outwardly from the central ring 18 of the anatomic plate 12. In particular, each flange 20 extends from a predetermined position 28 on the central ring 18 to a flange end 30. A flange length 32 is defined between the central ring 18 and the flange end 30. Each flange has a generally flat shape, and the proximal surface 14 of each flange 20 is configured to engage or otherwise intimately contact the patient's bone. In some embodiments, each flange 20 may include a Porocoat® outer coating 34 that permits bone to affix biologically to the flange 20 after implantation. The Porocoat® outer coating 34 covers the proximal surface 14 of each flange 20 and follows its geometric shape. It should be appreciated that in other embodiments the Porocoat® outer coating 34 may be omitted. Each flange 20 may extend straight away from the central ring 18 or may extend at an angle from the central ring 18 in a proximal and/or distal direction. Each flange 20 may be rigid, or in some embodiments may be malleable. For example, in some embodiments a surgeon may be capable of manually bending a flange 20 in order to achieve intimate contact with the patient's bone.

As shown in FIGS. 1-2, the illustrative anatomic plate 12 includes two flanges 20, particularly an ilial flange 36 and an ischial flange 38. As described further below, the illial flange 36 is configured (e.g., with a position 28 and/or flange length 30) to contact the patient's ilium, and the ischial flange 38 is configured (e.g., with a position 28 and/or flange length 30) to contact the patient's ischium. The ilial flange 38 further includes multiple apertures 40 defined through the surfaces 14, 16. In use, screws, pins, or other fasteners may be inserted through the apertures 40 to secure the plate 12 to the patient's bone. Although illustrated in FIG. 1 as including two flanges 36, 38, it should be understood that in other embodiments, the plate 12 may include one flange 20, three flanges 20, or another number of flanges 20. Additionally, in other embodiments the flanges 20 may include a different number or arrangement of apertures 40 or other fixation guides to allow the plate 12 to be secured to the patient's bone.

As described above, the prosthetic system 10 further includes the acetabular prosthetic shell component 42, which is shaped to be implanted in a surgically-prepared acetabulum of a patient's pelvis. The shell component 42 is formed from an implant-grade metallic material such as cobalt chromium or titanium. The shell component 42 has a distal rim 44 and an outer wall 46 that extends from the distal rim 44. The outer wall 46 includes an annular outer surface 48 that extends from the distal rim 44 to a convex curved outer surface 50. In the illustrative embodiment, the convex curved outer surface 50 is semi-spherical and shaped to match the shape of a patient's surgical prepared acetabulum. The shell component 42 also includes a Porocoat® outer coating 52 that permits bone to affix biologically to the shell component 42 after implantation. The Porocoat® outer coating 52 covers the outer surface 50 and follows its geometric shape. It should be appreciated that in other embodiments the Porocoat® outer coating 52 may be omitted.

A lip 54 is positioned on the annular outer surface 48, between the distal rim 44 and the convex outer surface 50. The lip 54 extends outwardly away from the annular outer surface 48, and includes a distal surface 56 positioned opposite a proximal surface 58. Multiple apertures 60 are defined in the lip 54. The apertures 60 are positioned on the lip 54 in positions that correspond to the apertures 26 of the anatomic plate 12. Also similar to the apertures 26, each of the apertures 60 are configured to receive a fastener. For example, in some embodiments, each aperture 60 may include a threaded inner wall that is configured to mate with a threaded body of a screw. As described further below, the apertures 26, 60 and corresponding fasteners may be used to mechanically attach the plate 12 to the shell component 42.

As shown, the distal surface 56 of the lip 54 is spaced apart from distal rim 44 by a distance 62. The distance 62 may determine the degree of lateralization of the shell component 42. That is, the distance 62 between the lip 54 and the distal rim 44 may determine the medial/lateral position of the center of rotation defined by the acetabular shell component 42. As described further below, in use a surgeon may select the shell component 42 from among multiple shell components 42 that each have a different lateralization distance 62.

Additionally as shown, an imaginary plane 64 is defined by extending the surface of the distal rim 44. Similarly, an imaginary plane 66 is defined by the lip 54, more particularly by extending the distal surface 56 of the lip 54. An angle 68, which may be zero or nonzero, is defined between the imaginary planes 64, 66. When the shell component 42 is attached to the plate 12, the angle 68 may determine the relative angle between the surface of the distal rim 44 and the plate 12. As described further below, in use this angle may determine the inclination, the version, or otherwise determine the orientation of distal rim 44 relative to the patient's hip. As described further below, in use a surgeon may select the shell component 42 from among multiple shell components 42 that each have a different angle 68.

The shell component 42 further includes an inner wall 70 that extends inwardly from the distal rim 44 to define a cavity 72 in the shell component 42. The illustrative cavity 72 is sized to receive a bearing component (not shown), which may be formed from a polymeric material such as, for example, polyethylene, a ceramic material, a metallic material, or other material. The inner wall 70 of the shell component 42 includes an annular inner surface 74 that is positioned opposite the annular outer surface 48, and a concave curved inner surface 76 that is opposite the convex curved outer surface 50. A plurality of slots 78 extend outwardly from the inner wall 70 of the distal rim 44. The slots 78 are spaced apart around the circumference of the distal rim 44 and are shaped to receive corresponding keys of the bearing and/or other prosthetic component. The concave curved inner surface 76 defines a polar axis 80 extending through the cavity 72. The polar axis 80 is normal to the plane 64 defined by the distal rim 44. In some embodiments, the polar axis 80 may be non-normal to the plane 66 defined by the lip 54, for example in embodiments with a nonzero angle 68. In some embodiments, one or more slots 82 or other fixation guides may be defined through the curved surfaces 50, 76. In use, screws, pins, or other fasteners may be inserted through the fixation guides 82 to secure the shell component to the patient's bone.

As described above, multiple apertures 26 are defined in the central ring 18 of the anatomic plate 12. For each aperture 26, a corresponding aperture 60 is defined in the lip 54 of the shell component 42. As shown, multiple screws 84 may be used to secure the central ring 18 to the lip 54. In particular, each screw 84 passes through a pair of corresponding apertures 26, 60, which mechanically attaches the plate 12 to the shell component 42. Although illustrated as being attached using multiple screws 84, it should be understood that in some embodiments the plate 12 and the shell component 42 may be attached using pins, rivets, or any other appropriate fastener.

Referring now to FIG. 3, a cross-sectional view of the prosthetic system 10 illustrates the distance 62 defined between the distal rim 44 and the distal surface 56 of the lip 54. In the illustrative embodiment, the distance 62 is two millimeters. It should be understood that other shell components included in the prosthetic system 10 may define different lateralization distances 62.

Figure 4:
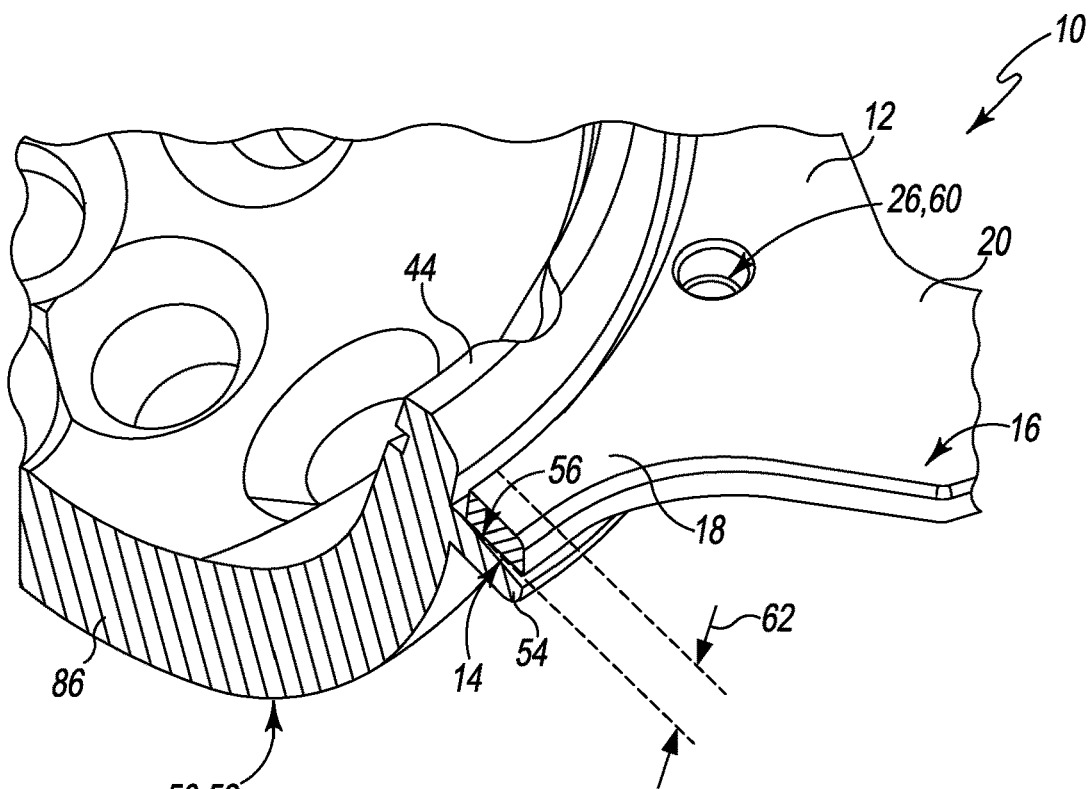
FIG. 4 is a cross-sectional perspective view of an assembled orthopaedic prosthetic system of FIG. 1 having a different lateralization.

For example, and referring now to FIG. 4, a cross-sectional view of another prosthetic system 10 shows the anatomic plate 12 secured to another acetabular shell component 86. The acetabular shell component 86 is similar to the shell component 42 shown in FIGS. 1-3; however, in the illustrative embodiment, the distance 62 defined between the distal rim 44 and the distal surface 56 of the shell component 86 is four millimeters. Accordingly, the center of rotation defined by the shell component 86 may be lateralized by two millimeters (i.e., moved two millimeters in a lateral direction) as compared to the center of rotation defined by the acetabular shell component 42.

Similarly, it should be understood that shell components included in the prosthetic system 10 may define different inclination angles 68. For example, referring now to FIG. 5, a cross-sectional view of another prosthetic system 10 shows the anatomic plate 12 secured to another acetabular shell component 88. The acetabular shell component 88 is similar to the shell components 42, 86 shown in FIGS. 1-4; however, in the illustrative embodiment, the angle 68 of the shell component 88 defined between the imaginary plate 64 defined by the distal rim 44 and the imaginary plane 66 defined by the lip 54 is non-zero. Additionally and as a result, the distance 62 between the distal rim 44 and the distal surface 56 of the lip 54 varies. In the illustrative embodiment, the distance 62 at its largest point is two millimeters, similar to the acetabular shell component 42. The position of this largest point relative to the plate 12 may be adjusted by rotating the shell component 88 relative to the plate 12 before securing the shell component 88 to the plate 12 with the screws 84 or other fasteners.

Figures 5, 6:
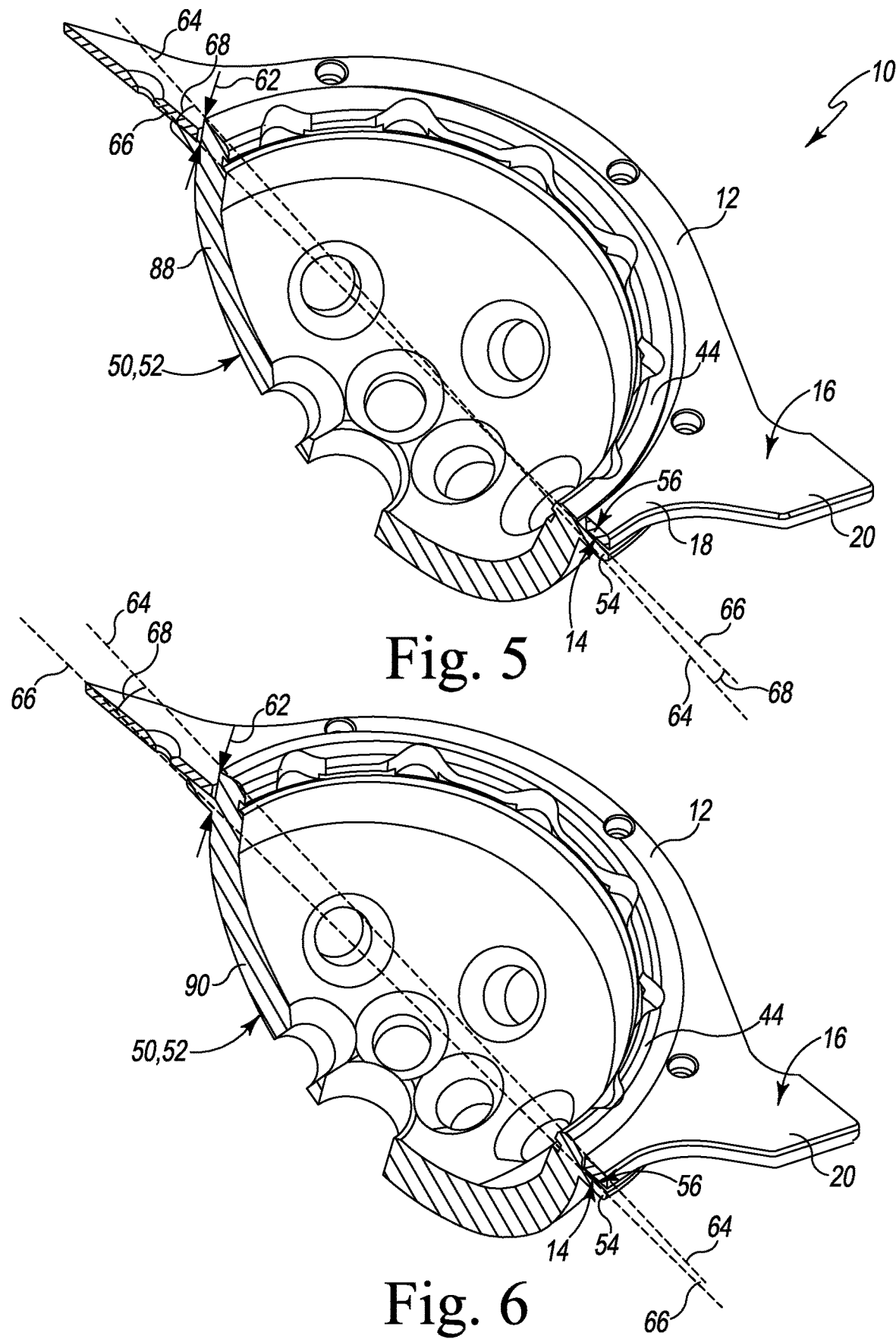
FIG. 5 is a cross-sectional perspective view of an assembled orthopaedic prosthetic system of FIG. 1 having a different inclination angle.
FIG. 6 is a cross-sectional perspective view of an assembled orthopaedic prosthetic system of FIG. 1 having a different lateralization and a different inclination angle.

As a further example, referring now to FIG. 6, a cross-sectional view of another prosthetic system 10 shows the anatomic plate 12 secured to another acetabular shell component 90. The acetabular shell component 90 is similar to the shell components 42, 86, 88 shown in FIGS. 1-5. Illustratively, the angle 68 of the shell component 90 defined between the imaginary plane 64 defined by the distal rim 44 and the imaginary plane 66 defined by the lip 54 is non-zero, similar to the shell component 88. In the illustrative embodiment, the distance 62 between the distal rim 44 and the distal surface 56 at its largest point is four millimeters, similar to the acetabular shell component 86. Thus, the illustrative shell components 42, 86, 88, 90 represent multiple potential combinations of lateralization distance 62 and inclination angle 68. Additionally or alternatively, in some embodiments other configurations such as size may also vary between acetabular shell components.

Figure 7:
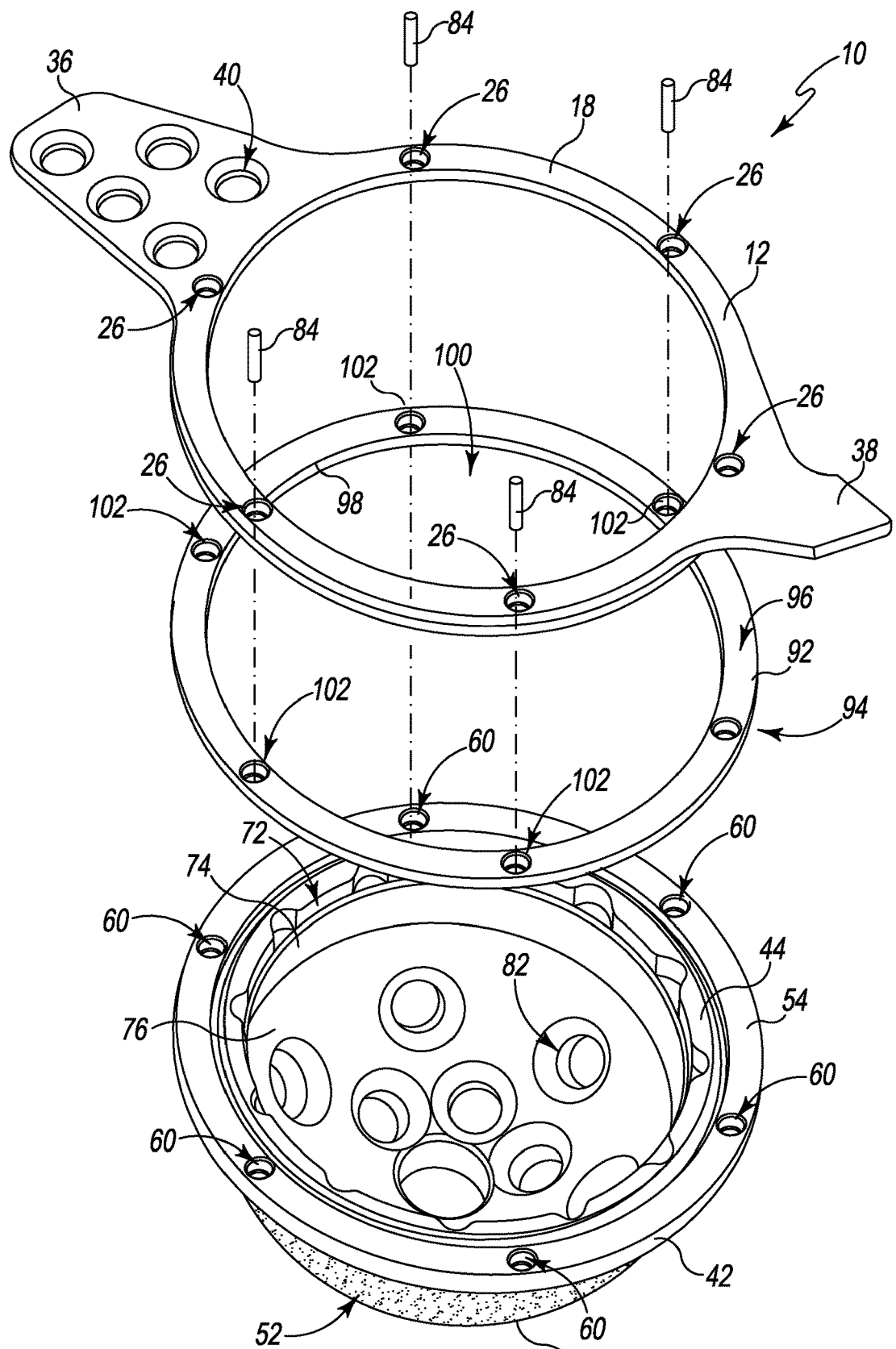
FIG. 7 is an exploded perspective view of the orthopaedic prosthetic system of FIG. 1 including a ring spacer.
Figure 8:
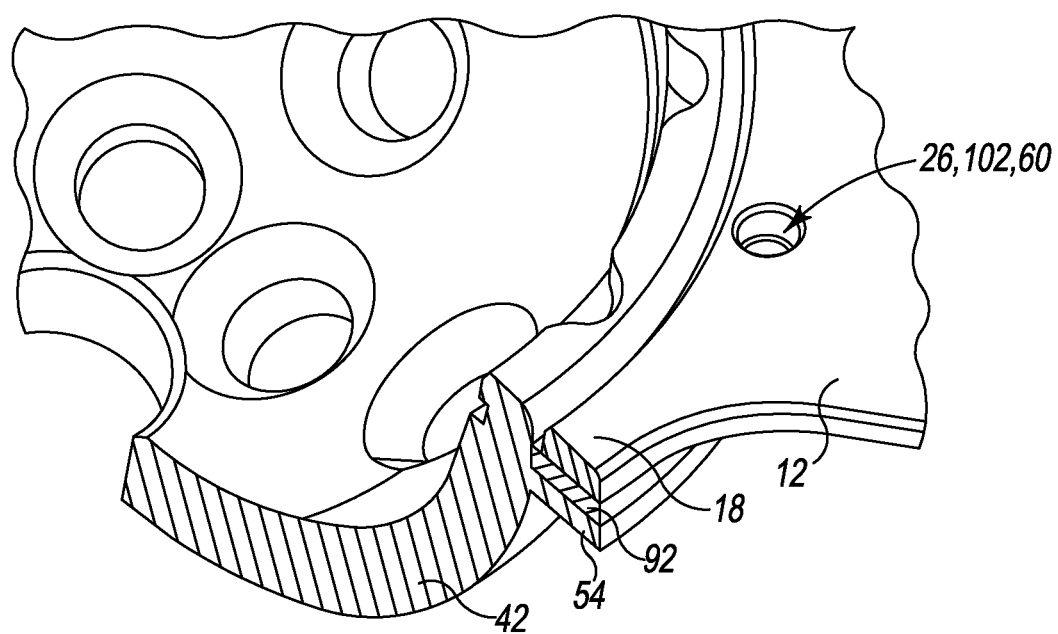
FIG. 8 is a cross-sectional perspective view of an assembled orthopaedic prosthetic system of FIG. 8.

Referring now to FIGS. 7 and 8, in some embodiments, the acetabular prosthetic implant system 10 may also include a ring spacer 92 that may be attached between the lip 54 of the acetabular shell component 42 and the central ring 18 of the anatomic plate 12. Similar to the shell component 42 and the plate 12, the ring spacer 92 is formed from an implant-grade metallic material such as cobalt chromium or titanium. As shown, the ring spacer 92 includes a proximal surface 94 spaced apart from a distal surface 96. An inner wall 98 extends between the surfaces 94, 96 and defines an opening 100. The opening 100 is sized to receive part of the acetabular shell component 42. Multiple apertures 102 are defined through the surfaces 94, 96. The apertures 102 are each configured to receive a fastener. For example, in some embodiments, each aperture 102 may include a threaded inner wall that is configured to mate with a threaded body of a screw. As shown, each aperture 102 aligns with corresponding apertures 26, 60 defined in the plate 12 and the shell component 42, respectively. Those apertures 26, 102, 60 and corresponding fasteners may be used to mechanically attach the spacer 92 between the plate 12 and the shell component 42. By attaching the spacer 92 between the plate 12 and the shell component 42, the proximal surface 14 of the plate 12 may be moved toward the distal rim 44 of the shell component 42 by the thickness of the spacer ring 92. Thus, by attaching the spacer ring 92 to the prosthetic system 10, the surgeon may adjust the amount of lateralization of the assembled prosthetic system 10.

Figure 9:
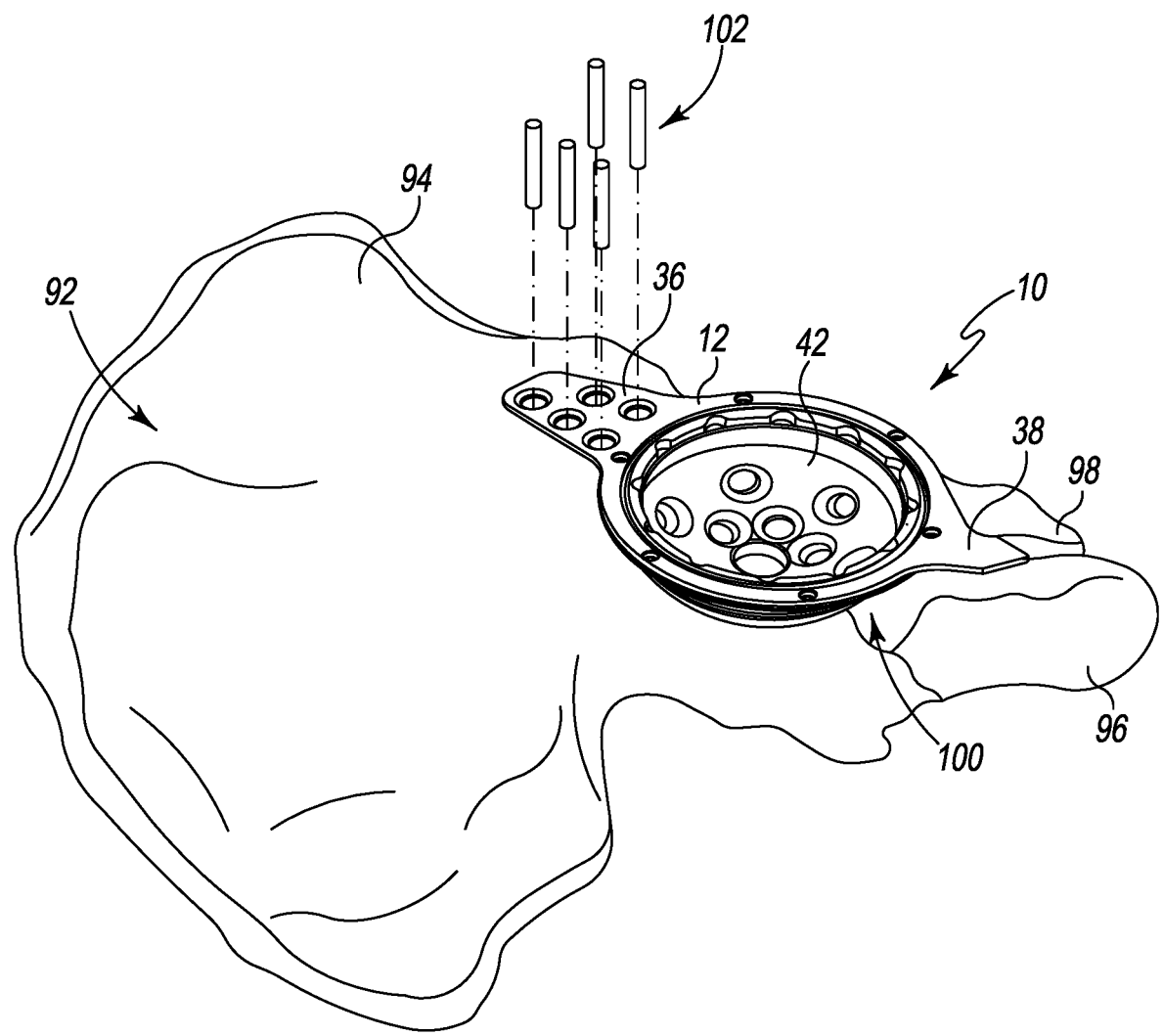
FIG. 9 is a perspective view showing the acetabular shell component of FIGS. 1-3 installed in a patient's hip.

Referring now to FIG. 9, in use, the orthopaedic prosthetic system 10 may be used during an orthopaedic surgical procedure. FIG. 9 illustrates a patient's hip bone 104. As shown, the hip bone 104 includes three parts, an ilium 106, an ischium 108, and a pubis 110, that define a natural acetabulum 112. To perform the orthopaedic surgical procedure, first, the surgeon surgically prepares the patient's bone to receive the prosthetic assembly 10. For example, the surgeon may utilize a surgical reamer to prepare the patient's acetabulum 112 to receive the prosthetic assembly 10. In some embodiments, the surgeon may also remove any existing acetabular component or other prosthetic components from the patient's bone.

The surgeon next selects an anatomic plate 12 from multiple available anatomic plates 12. Each of those anatomic plates 12 has a different configuration from the other anatomic plates 12. For example, each of the anatomic plates 12 may have a different number and/or arrangement of flanges 20, a different handedness (e.g., left/right), or other configuration. Continuing that example, the flanges 20 of each anatomic plate 12 may have a different predetermined position 28 relative to the central ring 18 or a different flange length 32.

After selecting the anatomic plate 12, the surgeon selects an acetabular shell component 42 from multiple available shell components 42. Each of those shell components 42 has a different configuration from the other shell components 42. For example, each of the acetabular shell components 42 may have a different combination of lateralization distance 62 and/or inclination angle 68.

Next, the surgeon mechanically attaches the selected anatomic plate 12 to the selected acetabular shell component 42. The surgeon may position the central ring 18 of the plate 12 on the lip 54 of the acetabular shell component 42 and secure the central ring 18 to the lip 54 using multiple screws 84 or other fasteners. Particularly for inclined shell components 42 (e.g., shell components 42 with a nonzero inclination angle 68), the surgeon may rotate the shell component 42 relative to the anatomic plate 12 to achieve a desired orientation prior to securing the plate 12 to the shell component 42.

Additionally or alternatively, in some embodiments prior to attaching the anatomic plate 12 to the acetabular shell component 42, the surgeon may select a spacer ring 92. In those embodiments, the surgeon may position the spacer ring 92 on the lip 54 of the acetabular shell component 42, position the central ring 18 of the plate 12 on the spacer ring 92, and then secure the central ring 18 to the spacer ring 92 and the lip 54 using multiple screws 84 or other fasteners.

The surgeon next inserts the shell component 42 of the assembled prosthetic system 10 into the patient's surgically prepared acetabulum 112 until the flanges 20 of the anatomic plate 12 contact the patient's bone 104. For example, in the illustrative embodiment, the ilial flange 36 contacts the ilium 106 and the ischial flange 38 contacts the ischium 108. The surgeon may assess whether intimate contact is achieved between the flanges 20 and the bone 104 or otherwise assess stability of the prosthetic implant 10 in the bone 104. In some embodiments, the surgeon may manually bend or otherwise adjust one or more of the flanges 20 in order to achieve intimate contact with the bone 104. Additionally or alternatively, in some embodiments the surgeon may remove the prosthetic system 10, select a different anatomic plate 12 and/or acetabular shell component 42, and re-assemble the prosthetic system 10 as described above to improve fit or otherwise improve fixation.

After positioning the prosthetic system 10 in the surgically prepared acetabulum 112, the prosthetic system 10 is impacted or otherwise fixed into a final position and orientation. In some embodiments, one or more bone screws 114 or other fasteners may be used to attach the flanges 20 to the bone 104. For example, in the illustrative embodiment, the bone screws 114 may be used to secure the ilial flange 36 to the ilium 106. Accordingly, after implantation, the prosthetic system 10 may be securely attached or otherwise fixed to solid bone of the patient, and may avoid attachment to diseased bone, voids, or other areas of bone loss surrounding the patient's acetabulum 112. The prosthetic system 10 may thus achieve a high degree of strength and may avoid the use of bone cement.

Figure 10:
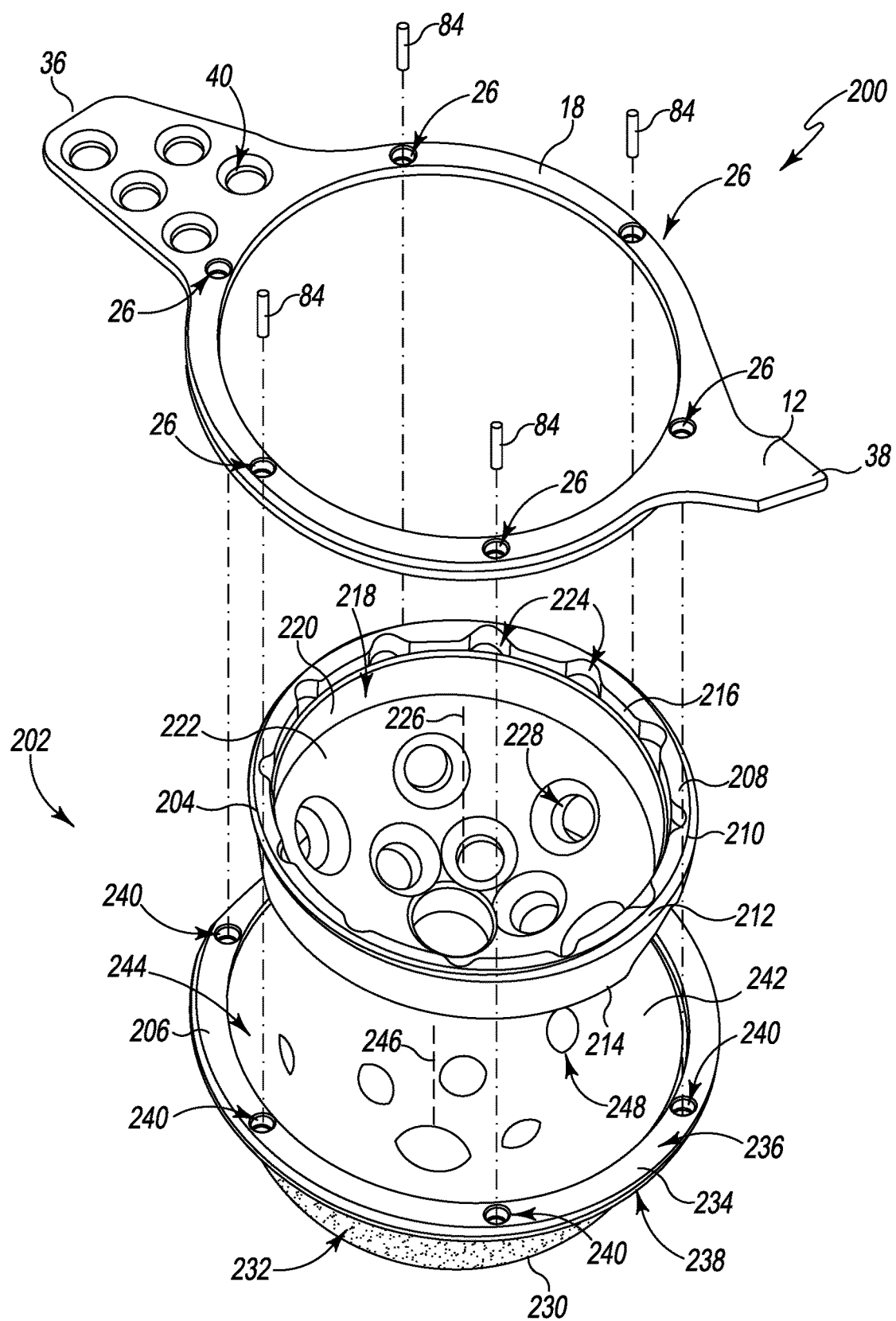
FIG. 10 is an exploded perspective view of another orthopaedic prosthetic system for an acetabular prosthetic implant including a two-part shell component.
Figure 11:
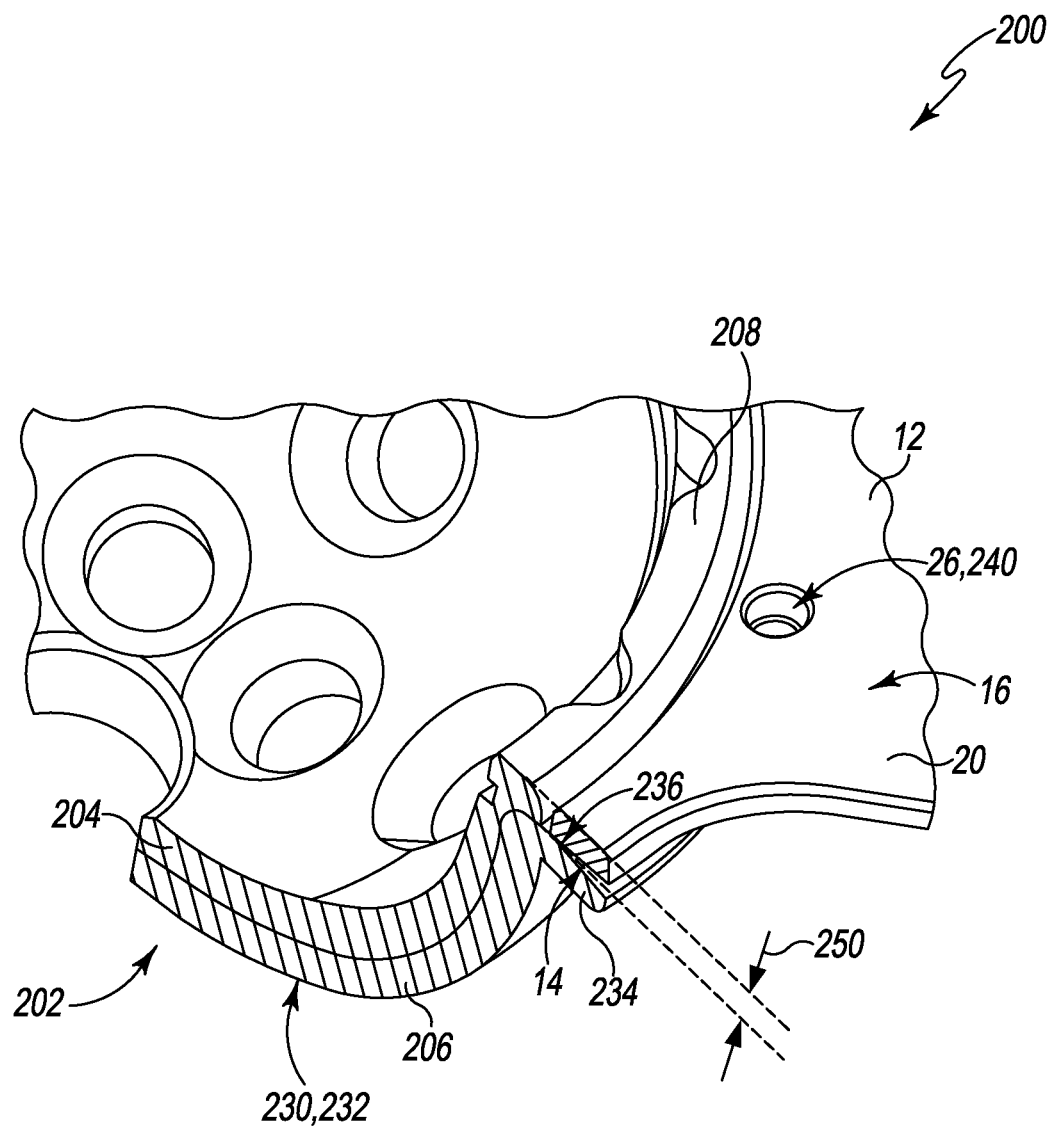
FIG. 11 is a cross-sectional perspective view of an assembled orthopaedic prosthetic system of FIG. 10.

Referring now to FIGS. 10-11, another illustrative acetabular prosthetic implant system 200 may be used during the orthopaedic surgical procedure described above in addition to or as an alternative to the prosthetic implant system 10. The prosthetic implant system 200 includes an anatomic plate 12 similar to the anatomic plate of FIGS. 1-9 and an acetabular shell component 202. Similar to the shell component 42 of FIGS. 1-3, the shell component 202 is shaped to be implanted in a surgically-prepared acetabulum of a patient's pelvis. Unlike the shell component 42, the shell component 202 is formed from two subcomponents 204, 206 that are mechanically attached to form the shell component 202. Each of the subcomponents 204, 206 is formed from an implant-grade metallic material such as cobalt chromium or titanium.

The inner subcomponent 204 has a distal rim 208 and an outer wall 210 that extends from the distal rim 208. The outer wall 210 includes an annular outer surface 212 that extends from the distal rim 208 to a convex curved outer surface 214. The convex curved outer surface 214 may be tapered or otherwise shaped to mate with a corresponding inner surface of the outer subcomponent 206, which is described further below.

The inner subcomponent 204 further includes an inner wall 216 that extends inwardly from the distal rim 208 to define a cavity 218 in the inner subcomponent 204. The illustrative cavity 218 is sized to receive a bearing component (not shown), which may be formed from a polymeric material such as, for example, polyethylene, a ceramic material, a metallic material, or other material. The inner wall 216 of the inner subcomponent 204 includes an annular inner surface 220 that is positioned opposite the annular outer surface 212, and a concave curved inner surface 222 that is positioned opposite the convex curved outer surface 214. A plurality of slots 224 extend outwardly from the inner wall 216 of the distal rim 208. The slots 224 are spaced apart around the circumference of the distal rim 208 and are shaped to receive corresponding keys of the bearing and/or other prosthetic component. The concave curved inner surface 222 defines a polar axis 226 extending through the cavity 218. The polar axis 226 is illustratively normal to an imaginary plane defined by the distal rim 208. In some embodiments, one or more slots 228 or other fixation guides may be defined through the curved surfaces 214, 222.

As shown, the outer subcomponent 206 also includes a convex curved outer surface 230. In the illustrative embodiment, the convex curved outer surface 230 is semi-spherical and shaped to match the shape of a patient's surgical prepared acetabulum. The outer subcomponent may also include a Porocoat® outer coating 232 that permits bone to affix biologically to the shell component 202 after implantation. The Porocoat® outer coating 232 covers the outer surface 230 and follows its geometric shape. It should be appreciated that in other embodiments the Porocoat® outer coating 232 may be omitted.

A lip 234 surrounds the convex curved outer surface 230. The lip 234 extends outwardly away from the curved outer surface 230, and includes a distal surface 236 positioned opposite a proximal surface 238. Multiple apertures 240 are defined in the lip 234. The apertures 240 are positioned on the lip 234 in positions that correspond to the apertures 26 of the anatomic plate 12. Also similar to the apertures 26, each of the apertures 240 are configured to receive a fastener. For example, in some embodiments, each aperture 240 may include a threaded inner wall that is configured to mate with a threaded body of a screw. As described further below, the apertures 26, 240 and corresponding fasteners may be used to mechanically attach the plate 12 to the shell component 202.

The outer subcomponent 206 further includes an inner wall 242 that extends inwardly from the lip 234 to define a cavity 244 in the outer subcomponent 206. The illustrative cavity 244 is sized to receive the inner subcomponent 204. Accordingly, the inner wall 242 is shaped to engage the convex outer surface 214 of the inner subcomponent 202. In some embodiments, the inner wall 242 may include a taper or other shape configured to mechanically lock with the outer surface 214 of the inner subcomponent 202. The inner wall 242 further defines a polar axis 246 extending through the cavity 244. In some embodiments, one or more slots 248 or other fixation guides may be defined through the inner wall 242 and the outer surface 230. As described further below, after assembly of the shell component 202, screws, pins, or other fasteners may be inserted through the fixation guides 228, 248 to secure the shell component 202 to the patient's bone.

As illustrated in a cross-sectional view in FIG. 11, the inner subcomponent 204 may be inserted into the cavity 244 defined in the outer subcomponent 206, thereby attaching the subcomponents 204, 206 together to form the acetabular shell component 202. When the subcomponents 204, 206 are attached together, the distal surface 236 of the lip 234 is spaced apart from distal rim 218 by a distance 250. The distance 250 may determine the degree of lateralization of the assembled shell component 202. That is, similar to the distance 62, the distance 250 determine the medial/lateral position of the center of rotation defined by the acetabular shell component 202. In use a surgeon may select the subcomponents 204, 206 from among multiple subcomponents 204, 206 in order to assemble a shell component 202 with a particular lateralization distance 250. In the illustrative embodiment shown in FIG. 11, the distance 250 is two millimeters. It should be understood that other shell components 202 included in the prosthetic system 200 may define different lateralization distances 250.

Additionally as shown, each of the inner subcomponent 204 and the outer subcomponent 206 define a polar axis 226, 246, respectively. An angle 252, which may be zero or nonzero is defined between the polar axes 226, 246. The angle 252 may determine the relative angle between the surface of the distal rim 208 and the plate 12. In use, this angle may determine the inclination, the version, or otherwise determine the orientation of distal rim 208 relative to the patient's hip. As described further below, in use a surgeon may select the subcomponents 204, 206 from among multiple subcomponents 204, 206 to assemble a shell components 202 that each has a particular angle 252.

Figure 12:
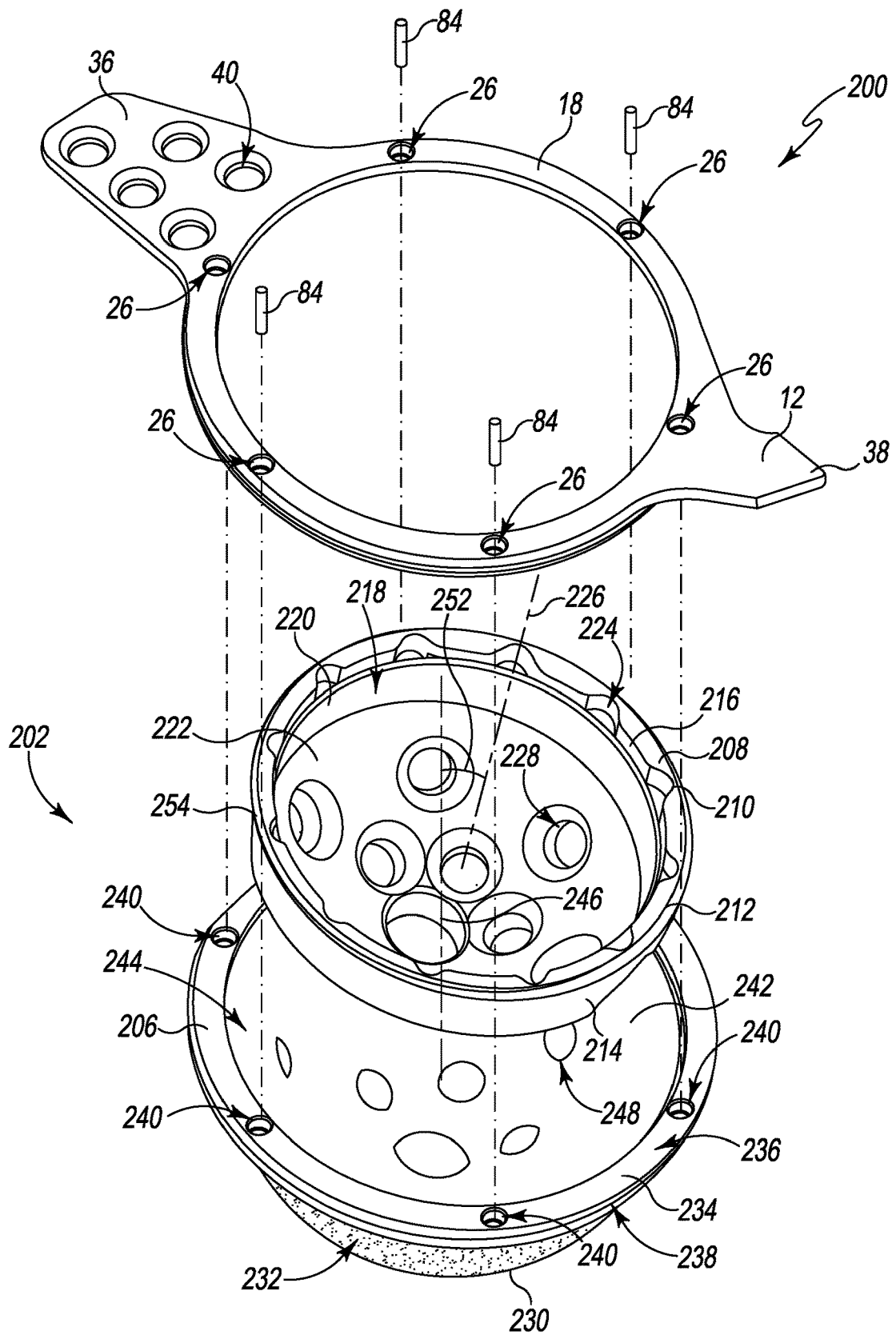
FIG. 12 is an exploded perspective view of the orthopaedic prosthetic system of FIG. 10 include a different inclination angle.
Figure 13:
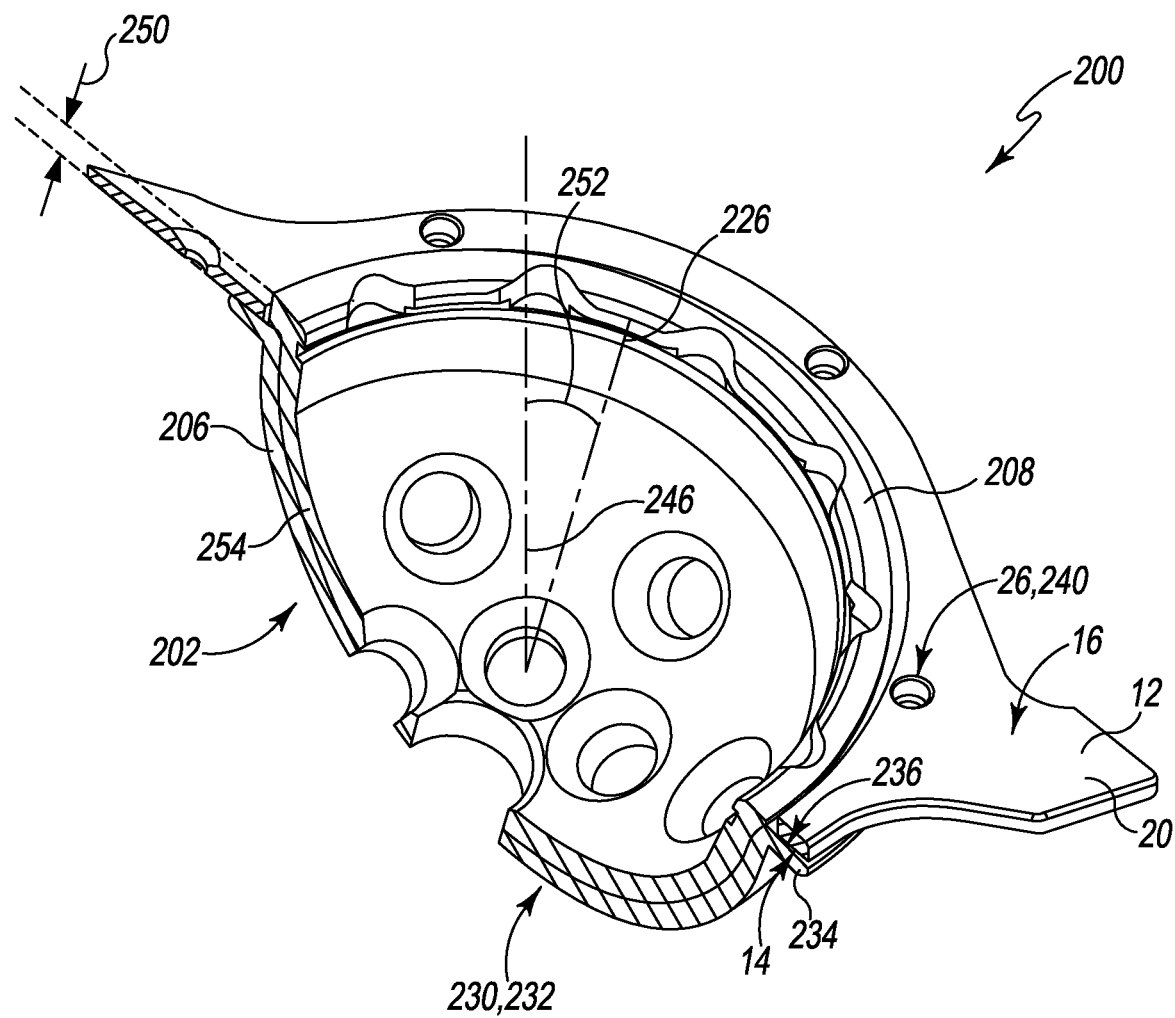
FIG. 13 is a cross-sectional perspective view of an assembled orthopaedic prosthetic system of FIG. 12.

For example, referring now to FIGS. 12 and 13, another prosthetic system 200 includes an acetabular shell component 202 formed from the outer subcomponent 206 and an inner subcomponent 254. The inner subcomponent 254 is similar to the inner subcomponent 204 shown in FIGS. 10-11; however, in the illustrative embodiment, when assembled with the outer subcomponent 206, a nonzero angle 252 is defined between the polar axis 226 of the inner subcomponent 254 and the polar axis 246 of the outer subcomponent 206. Additionally and as a result, the distance 250 between the distal rim 208 and the distal surface 236 of the lip 234 varies. In the illustrative embodiment, the distance 250 at its largest point is two millimeters, similar to the acetabular shell components 42, 88. The position of this largest point relative to the plate 12 may be adjusted, for example, by rotating the inner subcomponent 254 relative to the outer subcomponent 206 before assembling the plate 12 before assembling the shell component 202.

Figure 14:
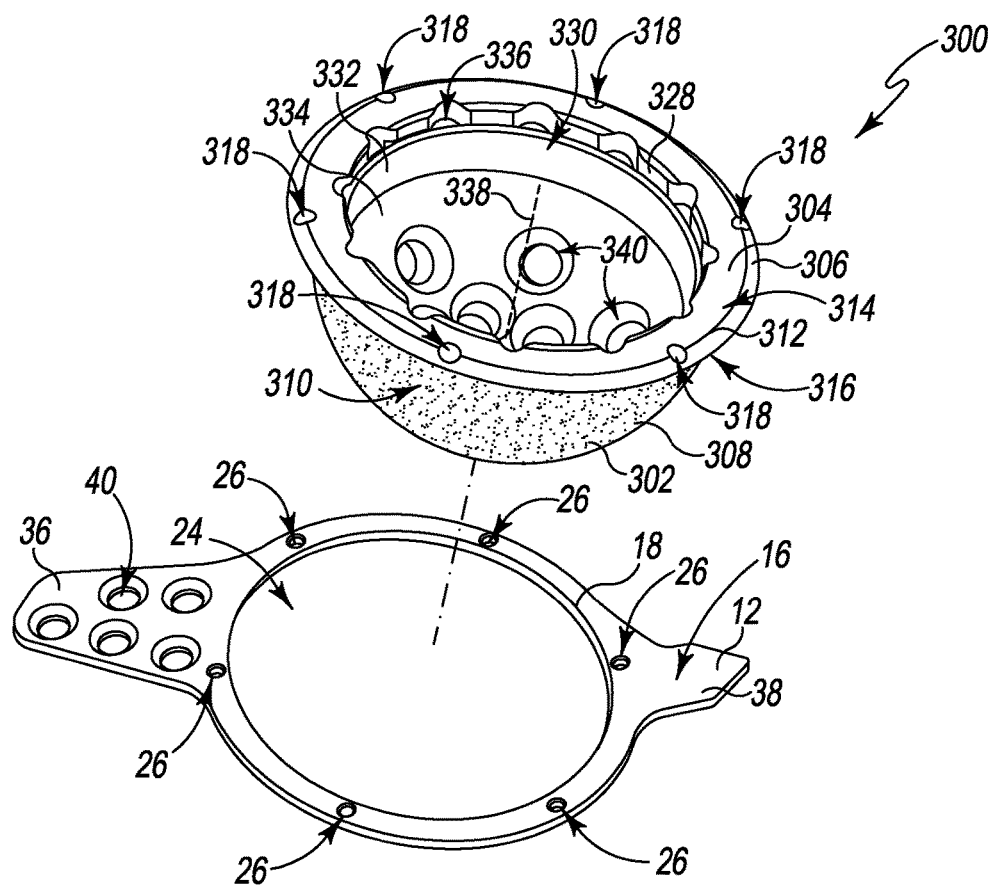
FIG. 14 is an exploded perspective view of another embodiment of an orthopaedic prosthetic system for an acetabular prosthetic implant.
Figure 15:
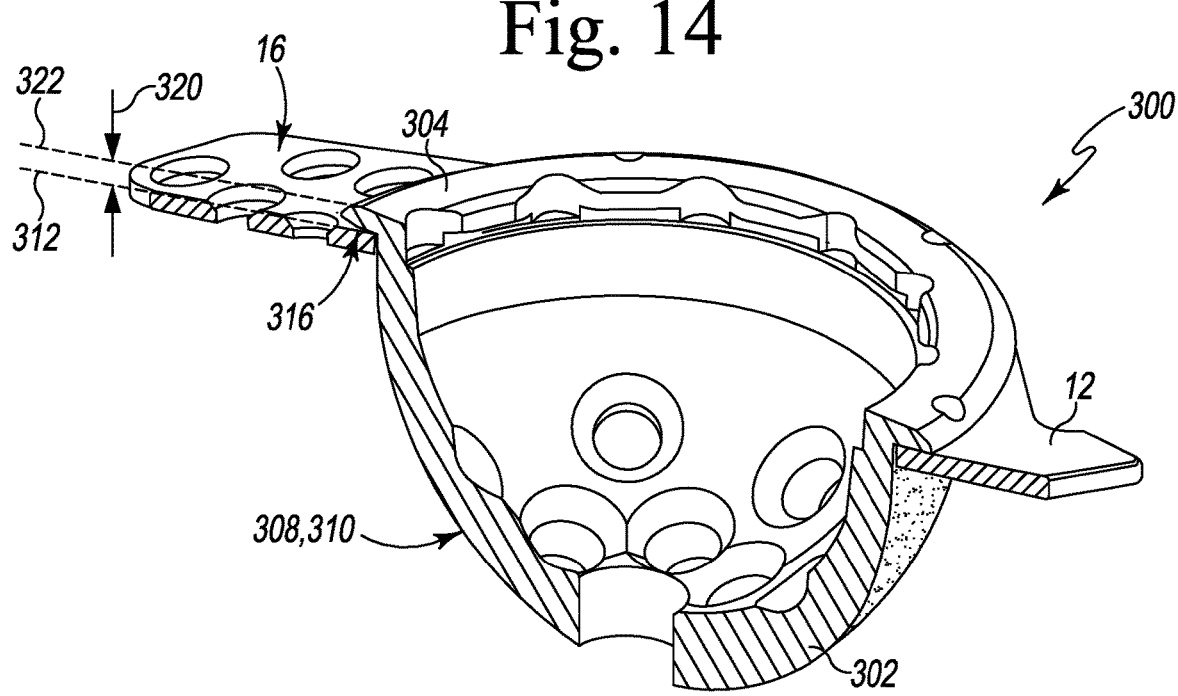
FIG. 15 is a cross-sectional perspective view of an assembled orthopaedic prosthetic system of FIG. 14.

Referring now to FIGS. 14 and 15, yet another embodiment of an acetabular prosthetic implant system 300 may be used during the orthopaedic surgical procedure described above in addition to or as an alternative to the prosthetic implant systems 10, 200. The prosthetic implant system 300 includes an anatomic plate 12 similar to the anatomic plate of FIGS. 1-13 and an acetabular shell component 302. Similar to the shell component 42 of FIGS. 1-3, the shell component 302 is shaped to be implanted in a surgically-prepared acetabulum of a patient's pelvis. The shell component 302 is formed from an implant-grade metallic material such as cobalt chromium or titanium. The shell component 302 has a distal rim 304 and an outer wall 306 that extends from the distal rim 304. The outer wall 306 includes a convex curved outer surface 308 that extends from the distal rim 304. In the illustrative embodiment, the convex curved outer surface 308 is semi-spherical and shaped to match the shape of a patient's surgical prepared acetabulum. The shell component 302 also includes a Porocoat® outer coating 310 that permits bone to affix biologically to the shell component 302 after implantation. The Porocoat® outer coating 310 covers the outer surface 308 and follows its geometric shape. It should be appreciated that in other embodiments the Porocoat® outer coating 310 may be omitted.

A lip 312 is positioned at the distal rim 304, extending outwardly away from the convex outer surface 308. The lip 312 includes a distal surface 314 at the distal rim 304 and further includes a proximal surface 316 positioned opposite the distal surface 314. Multiple apertures 318 are defined in the lip 312. The apertures 318 are positioned on the lip 312 in positions that correspond to the apertures 26 of the anatomic plate 12. Also similar to the apertures 26, each of the apertures 318 are configured to receive a fastener. For example, in some embodiments, each aperture 318 may include a threaded inner wall that is configured to mate with a threaded body of a screw. As described further below, the apertures 26, 318 and corresponding fasteners may be used to mechanically attach the plate 12 to the shell component 302.

As shown, the proximal surface 316 of the lip 312 is spaced apart from the distal rim 304 by a distance 320. The distance 320 may determine the degree of lateralization of the shell component 302. That is, the distance 320 between the proximal surface 316 of the lip 312 and the distal rim 304 may determine the medial/lateral position of the center of rotation defined by the acetabular shell component 302. In use, a surgeon may select the shell component 302 from among multiple shell components 302 that each have a different lateralization distance 320.

Additionally as shown, an imaginary plane 322 is defined by extending the surface of the distal rim 312. Similarly, an imaginary plane 324 is defined by the lip 312, more particularly by extending the proximal surface 316 of the lip 312. An angle 326, which may be zero or nonzero, is defined between the imaginary planes 322, 324. When the shell component 302 is attached to the plate 12, the angle 326 may determine the relative angle between the surface of the distal rim 304 and the plate 12. As described further below, in use this angle may determine the inclination, the version, or otherwise determine the orientation of distal rim 304 relative to the patient's hip. As described further below, in use a surgeon may select the shell component 302 from among multiple shell components 302 that each have a different angle 326.

The shell component 302 further includes an inner wall 328 that extends inwardly from the distal rim 304 to define a cavity 330 in the shell component 302. The illustrative cavity 330 is sized to receive a bearing component (not shown), which may be formed from a polymeric material such as, for example, polyethylene, a ceramic material, a metallic material, or other material. The inner wall 328 of the shell component 302 includes an annular inner surface 332 that is positioned opposite the lip 312, and a concave curved inner surface 334 that is opposite the convex curved outer surface 308. A plurality of slots 336 extend outwardly from the inner wall 328 of the distal rim 304. The slots 336 are spaced apart around the circumference of the distal rim 304 and are shaped to receive corresponding keys of the bearing and/or other prosthetic component. The concave curved inner surface 334 defines a polar axis 338 extending through the cavity 330. The polar axis 338 is normal to the plane 322 defined by the distal rim 304. In some embodiments, the polar axis 338 may be non-normal to the plane 324 defined by the lip 312, for example in embodiments with a nonzero angle 326. In some embodiments, one or more slots 340 or other fixation guides may be defined through the curved surfaces 308, 334. In use, screws, pins, or other fasteners may be inserted through the fixation guides to secure the shell component to the patient's bone.

As described above, multiple apertures 26 are defined in the central ring 18 of the anatomic plate 12. For each aperture 26, a corresponding aperture 318 is defined in the lip 312 of the shell component 302. As shown, the concave outer surface 308 of the shell component 302 may pass through the central opening 24 of the anatomic plate 12. The proximal surface 316 of the lip 312 engages the distal surface 16 of the anatomic plate 12 on the central ring 18. As shown, multiple screws 84 may be used to secure the central ring 18 to the lip 312. In particular, each screw 84 passes through a pair of corresponding apertures 26, 318, which mechanically attaches the plate 12 to the shell component 302. Although illustrated as being attached using multiple screws 84, it should be understood that in some embodiments the plate 12 and the shell component 302 may be attached using pins, rivets, or any other appropriate fastener.

Figure 16:
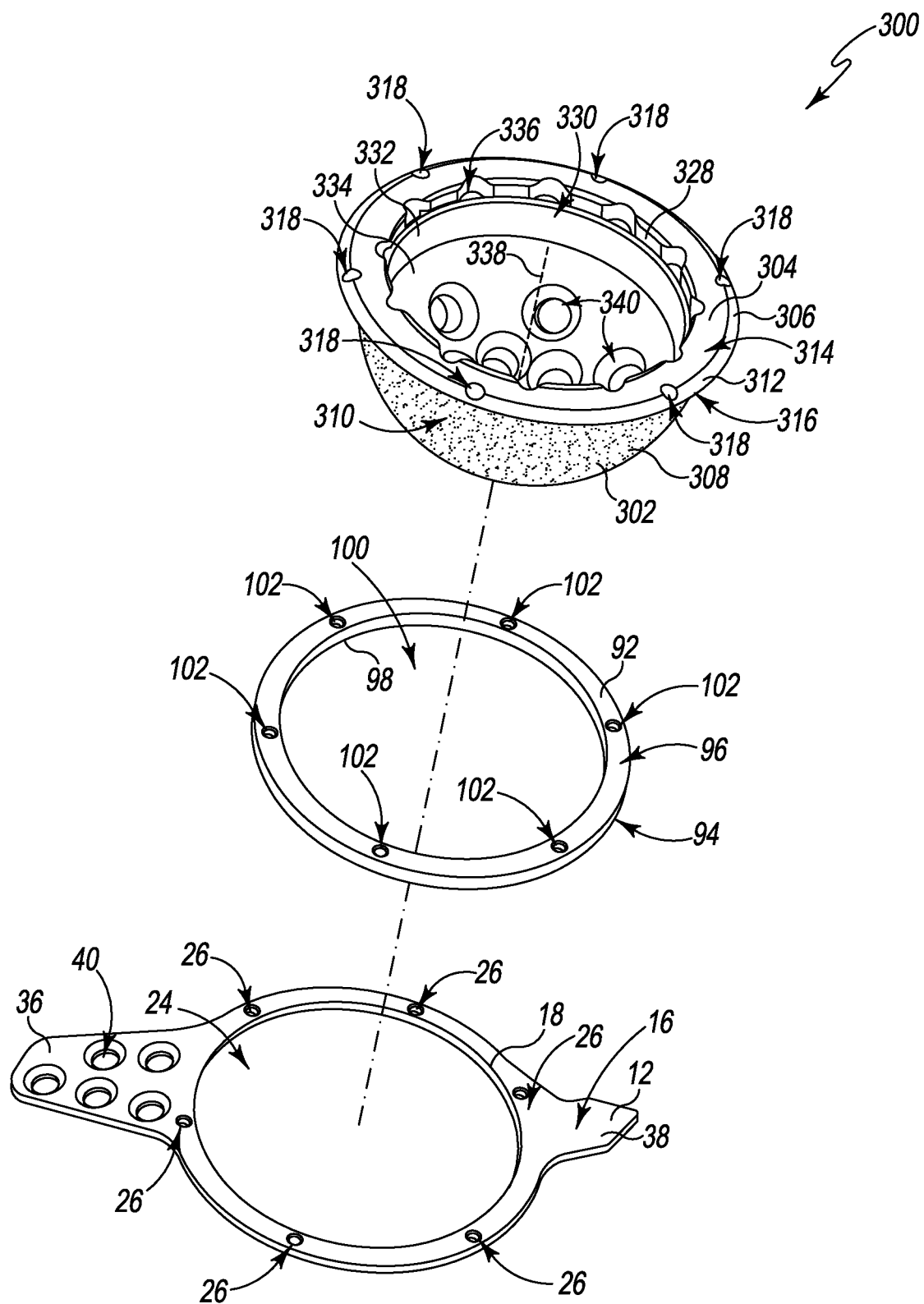
FIG. 16 is an exploded perspective view of the orthopaedic prosthetic system of FIG. 14 including a ring spacer.
Figure 17:
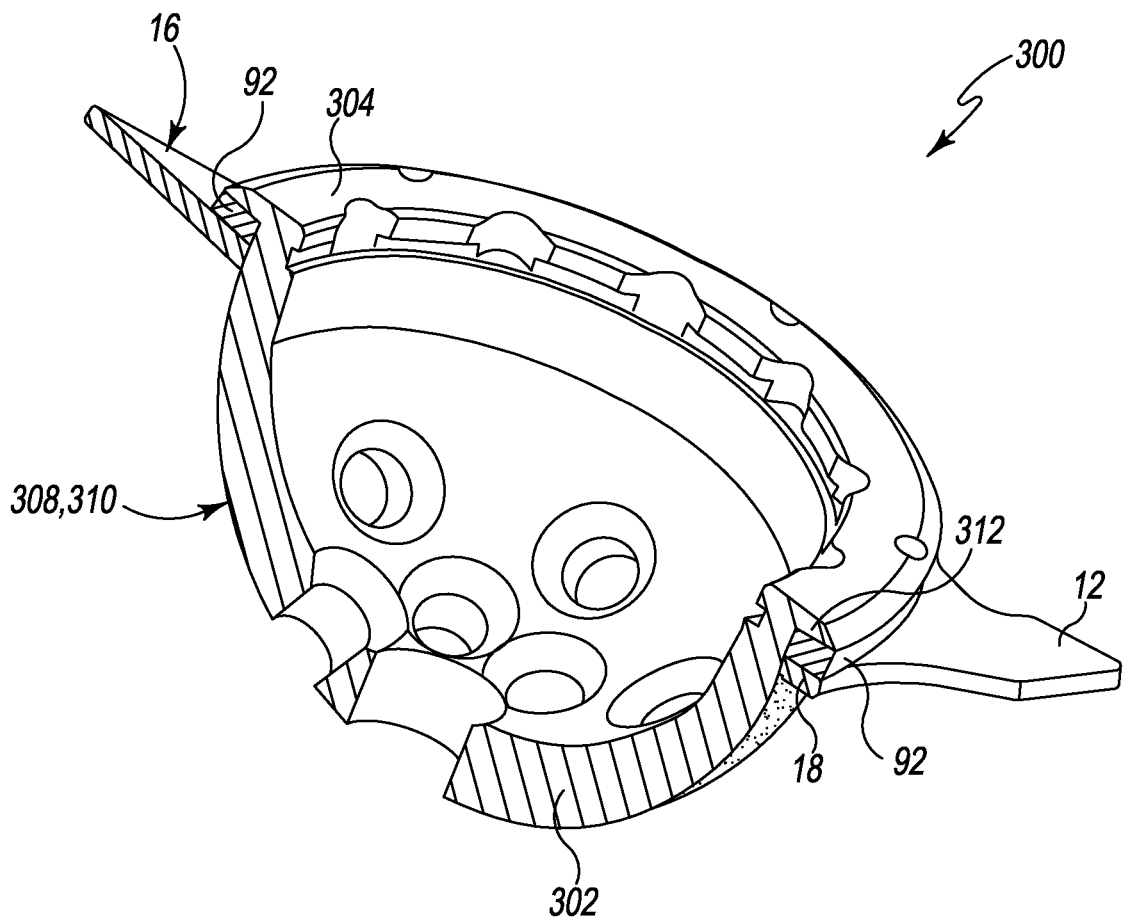
FIG. 17 is a cross-sectional perspective view of an assembled orthopaedic prosthetic system of FIG. 16.

Referring now to FIGS. 16 and 17, in some embodiments, the acetabular prosthetic implant system 300 may also include a ring spacer 92 similar to the ring spacer 92 shown in FIGS. 7 and 8. The ring spacer 92 may be attached between the lip 312 of the acetabular shell component 302 and the central ring 18 of the anatomic plate 12. A shown, the distal surface 96 of the ring spacer 92 engages the proximal surface 316 of the shell component 302, and the distal surface 16 of the anatomic plate 12 engages the proximal surface 94 of the ring spacer 92. The anatomic plate 12, the ring spacer 92, and the shell component 302 may be mechanically attached together using multiple screws 84 or other fasteners engaged through corresponding apertures 26, 102, 318. By attaching the spacer 92 between the plate 12 and the shell component 302, the proximal surface 14 of the plate 12 may be moved away from the distal rim 304 of the shell component 302 by the thickness of the spacer ring 92. Thus, by attaching the spacer ring 92 to the prosthetic system 300, the surgeon may adjust the amount of lateralization of the assembled prosthetic system 300.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic prosthetic system comprising:
a plate comprising a central ring and one or more flanges, wherein a plurality of apertures are defined in the central ring, and wherein each flange of the one or more flanges extends radially away from a corresponding predetermined position on the central ring, and wherein each of the one or more flanges includes a proximal surface to engage a patient's bone; and
an acetabular shell component comprising a distal rim, a convex outer wall extending from the distal rim, and a circumferential lip positioned on the outer wall and extending away from the outer wall, wherein the lip is separated from the distal rim by a lateralization distance, and wherein the lip defines a first imaginary plane and the distal rim defines a second imaginary plane, the first and second imaginary planes being non-parallel to each other to define an inclination angle therebetween that is greater than zero, and wherein a plurality of apertures are defined in the lip;
wherein the plate is configured to be positioned on the acetabular shell component such that each aperture of the central ring is aligned with a corresponding aperture of the lip of the acetabular shell component;
wherein when the plate is positioned on the acetabular shell component, a proximal surface of the central ring engages a distal surface of the lip, and the central ring receives the distal rim of the acetabular shell component; and
wherein the acetabular shell component comprises a concave curved inner wall that extends inwardly from the distal rim to define a hemispherical cavity sized to receive an acetabular bearing.

2. The orthopaedic prosthetic system of claim 1, further comprising a fastener that, when the plate is positioned on the acetabular shell component, extends through an aperture of the central ring into a corresponding aperture of the lip to secure the plate to the acetabular shell component.

3. The orthopaedic prosthetic system of claim 1, wherein the one or more flanges comprises an ilial flange configured to engage an ilium of the patient and an ischial flange configured to engage an ischium of the patient.

4. The orthopaedic prosthetic system of claim 1, wherein the plate is a first plate of a plurality of plates, each plate having a different configuration from other plates of the plurality of plates.

5. The orthopaedic prosthetic system of claim 4, wherein:
each flange of the one or more flanges of each plate extends radially away from the corresponding predetermined position on the central ring to a corresponding flange end, wherein a flange length is defined between the central ring and the flange end for each flange of the one or more flanges; and
the different configuration of each plate includes at least one of the flange length of one or more flange or the predetermined position on the central ring of one or more flange.

6. The orthopaedic prosthetic system of claim 1, wherein the acetabular shell component is a first shell component of a plurality of acetabular shell components, each acetabular shell component having a different configuration from other acetabular shell components of the plurality of acetabular shell components.

7. The orthopaedic prosthetic system of claim 6, wherein the different configuration of each acetabular shell component includes at least one of the lateralization distance or the inclination angle.

8. The orthopaedic prosthetic system of claim 1, wherein the proximal surface of each of the one or more flanges and the outer wall of the acetabular shell component includes a porous coating to promote bone ingrowth.

9. The orthopaedic prosthetic system of claim 1, wherein a flange of the one or more flanges comprises an aperture configured to receive a fastener to attach the flange to the patient's bone.

10. A method for assembling an orthopaedic prosthesis, the method comprising:
- selecting a first plate from a plurality of plates, wherein each plate of the plurality of plates comprises a central ring and one or more flanges, wherein each flange of the one or more flanges extends radially away from a corresponding predetermined position on the central ring, and wherein each of the one or more flanges includes a proximal surface to engage a patient's bone;
- selecting a first shell component from a plurality of acetabular shell components, wherein each acetabular shell component of the plurality of acetabular shell components comprises a distal rim, a convex outer wall extending from the distal rim, a concave curved inner wall that extends inwardly from the distal rim to define a hemispherical cavity sized to receive an acetabular bearing, and a circumferential lip positioned on the outer wall and extending away from the outer wall, and wherein the lip of each acetabular shell defines a first imaginary plane and the distal rim of each acetabular shell defines a second imaginary plane, the first and second imaginary planes being non-parallel to each other to define an inclination angle therebetween that is greater than zero; and
- mechanically attaching the lip of the first shell component to the central ring of the first plate, comprising engaging a proximal surface of the central ring of the first plate with a distal surface of the lip of the first shell component, wherein the central ring of the first plate receives the distal rim of the first shell component.

11. The method of claim 10, wherein:
- a plurality of apertures are defined in the central ring of each plate of the plurality of plates, and a plurality of apertures are defined in the lip of each acetabular shell component of the plurality of acetabular shell components; and
- mechanically attaching the lip of the first shell component to the central ring of the first plate comprises, for each aperture defined in the central ring, securing a fastener to the aperture of the central ring and to a corresponding aperture of the lip.

12. The method of claim 10, wherein mechanically attaching the lip of the first shell component to the central ring comprises (i) attaching a spacer ring to the central ring and (ii) attaching the spacer ring to the lip.

13. The method of claim 10, wherein selecting first shell component comprises:
- selecting a first subcomponent, wherein the first subcomponent comprises the outer wall and the lip of the first shell component;
- selecting a second subcomponent, wherein the second subcomponent comprises the distal rim and a concave inner wall that extends inwardly from the distal rim; and
- attaching the first shell subcomponent to the second shell subcomponent.

14. The method of claim 10, further comprising:
- inserting the first shell component into a surgically prepared acetabulum of a patient in response to mechanically attaching the lip of the first shell component to the central ring of the first plate; and
- contacting the one or more flanges of the first plate against the patient's bone in response to inserting the first shell component.

* * * * *